United States Patent
Ondrus et al.

(10) Patent No.: US 9,624,149 B2
(45) Date of Patent: Apr. 18, 2017

(54) PROCESS FOR PREPARING A CHLORINATED ALKENE

(71) Applicant: SPOLEK PRO CHEMICKOU A HUTNI VYROBU A.S., Usti nad Labem (CZ)

(72) Inventors: Zdenek Ondrus, Vrbice (CZ); Pavel Kubicek, Decin (CZ); Karel Filas, Usti nad Labem (CZ); Petr Sladek, Usti nad Labem-Strekov (CZ)

(73) Assignee: SPOLEK PRO CHEMICKOU A HUTNI VYROBU A.S., Usti nad Labem (CZ)

( * ) Notice: Subject to any disclaimer, the term of this patent is extended or adjusted under 35 U.S.C. 154(b) by 0 days.

(21) Appl. No.: 14/883,642

(22) Filed: Oct. 15, 2015

(65) Prior Publication Data
US 2016/0107960 A1    Apr. 21, 2016

(30) Foreign Application Priority Data
Oct. 16, 2014 (CZ) .............................. PV 2014-706

(51) Int. Cl.
C07C 17/25     (2006.01)
C07C 17/383    (2006.01)
C07C 17/38     (2006.01)
C07C 21/04     (2006.01)

(52) U.S. Cl.
CPC .............. *C07C 21/04* (2013.01); *C07C 17/25* (2013.01); *C07C 17/383* (2013.01)

(58) Field of Classification Search
CPC ...................................................... C07C 17/25
See application file for complete search history.

(56) References Cited

U.S. PATENT DOCUMENTS

| | | | |
|---|---|---|---|
| 4,650,914 A * | 3/1987 | Woodard | ................ C07C 17/04 570/220 |
| 7,094,936 B1 * | 8/2006 | Owens | .................... C07C 17/00 570/170 |
| 2014/0221705 A1 * | 8/2014 | Wang | ....................... C07C 17/10 570/220 |
| 2014/0228601 A1 * | 8/2014 | Dawkins | ................. C07C 17/38 570/230 |
| 2014/0275658 A1 | 9/2014 | Yang | |

FOREIGN PATENT DOCUMENTS

| | | |
|---|---|---|
| EP | 2447238 | 5/2012 |
| EP | 2646402 | 10/2013 |
| EP | 2687504 | 1/2014 |
| WO | WO-2009/085862 | 7/2009 |

* cited by examiner

*Primary Examiner* — Jafar Parsa
*Assistant Examiner* — Medhanit Bahta
(74) *Attorney, Agent, or Firm* — Pearl Cohen Zedek Latzer Baratz LLP

(57) ABSTRACT

Disclosed is a process for preparing a chlorinated alkene, comprising contacting a chlorinated alkane with a catalyst in a dehydrochlorination zone to produce a liquid reaction mixture comprising the chlorinated alkane and the chlorinated alkene, and extracting chlorinated alkene from the reaction mixture, wherein the concentration of the chlorinated alkene in the reaction mixture present in the dehydrochlorination zone is controlled such that the molar ratio of chlorinated alkene:chlorinated alkane is from 1:99 to 50:50.

26 Claims, 3 Drawing Sheets

PROCESS FOR PREPARING A CHLORINATED ALKENE

CROSS-REFERENCE TO RELATED APPLICATIONS

This application claims priority of Czech Patent Application No. PV 2014-706, filed Oct. 16, 2014, which is hereby incorporated by reference.

The present invention relates to processes for producing high purity chlorinated alkene compounds, such as 1,1,3-trichloropropene (1240za), 3,3,3-trichloropropene (1240zf), 1,1,3,3-tetrachloropropene (1230za), 1,1,2,3-tetrachloropropene (1230xa), 1,1,1,2-tetrachloropropene (1230xf), 1,1,2-trichloropropene, 1,1,2,3,3-pentachloropropene, 1,1,3,3,3-pentachloropropene and 1,1,2,3,3,3-hexachloropropene and also to compositions comprising such compounds.

Haloalkanes find utility in a range of applications. For example, halocarbons are used extensively as refrigerants, blowing agents and foaming agents. Throughout the second half of the twentieth century, the use of chlorofluoroalkanes increased exponentially until the 1980's, when concerns were raised about their environmental impact, specifically regarding depletion of the ozone layer.

Subsequently, fluorinated hydrocarbons such as perfluorocarbons and hydrofluorocarbons have been used in place of chlorofluoroalkanes, although more recently, environmental concerns about the use of that class of compounds have been raised and legislation has been enacted in the EU and elsewhere to reduce their use.

New classes of environmentally friendly halocarbons are emerging and have been investigated, and in some cases, embraced in a number of applications, especially as refrigerants in the automotive and domestic fields. Examples of such compounds include 1,1,1,2-tetrafluoroethane (R-134a), 2-chloro-3,3,3-trifluoropropene (HFO-1233xf), 1,3,3,3-tetrafluoropropene (HFO-1234ze), 3,3,3-trifluoropropene (HFO-1243zf), and 2,3,3,3-tetrafluoropropene (HFO-1234yf), 1,2,3,3,3-pentafluoropropene (HFO-1225ye), 1-chloro-3,3,3-trifluoropropene (HFO-1233zd), 3,3,4,4,4-pentafluorobutene (HFO-1345zf), 2,4,4,4-tetrafluorobut-1-ene (HFO1354mfy), 1,1,1,4,4,4-hexafluorobutene (HFO-1336mzz), 3,3,4,4,5,5,5-heptafluoropentene (HFO1447fz), and 1,1,1,4,4,5,5,5-octafluoropentene (HFO-1438mzz).

While these compounds are, relatively speaking, chemically non-complex, their synthesis on an industrial scale to the required levels of purity is challenging. Many synthetic routes proposed for such compounds increasingly use, as starting materials or intermediates, chlorinated alkanes or alkenes. The conversion of the chlorinated alkane or alkene starting materials to the fluorinated target compounds is usually achieved using hydrogen fluoride and transition metal catalysts, for example chromium-based catalysts.

It has been recognised that when the chlorinated feedstock is obtained from a multi-step process, especially if such steps are linked and run continuously to achieve industrially acceptable product volumes, then the need to prevent cumulative side reactions from generating unacceptable impurities at each process step is very important.

The purity of the chlorinated starting materials will have a substantial effect on the success and viability of the processes (especially continuous processes) for preparing the desirable fluorinated products. The presence of certain impurities will result in side reactions, minimising the yield of the target compound. Additionally, the presence of certain impurities will compromise catalyst life.

Chlorinated alkenes may be employed as starting materials or intermediates in processes for producing the haloalkanes discussed above. Methods for the preparation and use of such chlorinated alkenes are provided in International Patent Application No. WO2009/085862, European Patent Application No. EP2447238, European Patent Application No. EP2646402, and US Patent Publication No US2014/0275658.

One well established method for producing chlorinated alkenes is via a dehydrochlorination step in which a chlorinated alkane is converted to a chlorinated alkene.

One drawback with many dehydrochlorination processes operated to date is their reliance upon the use of alkaline hydroxide, which is not preferable due to the environmental concerns regarding the use of such materials in dehydrochlorination reactions. Further, it has been found that such processes are typically not economically viable.

In European Patent Application EP2687504, a process is disclosed which seeks to avoid the use of sodium hydroxide in a dehydrochlorination reaction. In that reaction, 1,1,1,3-tetrachloropropane is dehydrochlorinated to produce 1,1,3-trichloropropene which is then converted in situ to 1,1,1,2,3-pentachloropropane, preferably in the absence of sodium hydroxide.

However, the impurity profile of 1,1,1,2,3-pentachloropropane produced in that way is unfavourable and this stems, at least partly, from the production of impurities during the dehydrochlorination step. In other words, the in situ produced 1,1,3 trichloropropene intermediate has an unacceptable impurity profile, resulting in a downstream product (1,1,1,2,3-pentachloropropane) which also has an unacceptable impurity profile.

As can be seen from Examples 7 to 9 of that document, the obtained 1,1,1,2,3-pentachloropropane included 5.8% to 8.1% of tetrachloropropene, which is not the target chlorinated alkene intermediate in the process discussed therein, i.e. it arises as a result of low chlorinated alkene selectivity in the dehydrochlorination. Further, factoring in the 'heavies' contents in those examples (3.3% to 6.3%), this amounts to a loss to impurities of over 10% which is industrially unacceptable. Further, the extraction of the impurity 1,1,2,3-tetrachloropropene from 1,1,1,2,3-pentachloropropane is onerous.

In US Patent Publication No. US2014/0275658, a process is disclosed which employs a chloroalkane starting material necessarily containing a 'heavies' impurity, this impurity apparently resulting in a more selective process. The highest purity chloroalkane starting material employed in the processes disclosed in that application is 98.%. The preferred degree of conversion of chloroalkane to chloroalkene in the processes disclosed in US2014/0275658 is at least 60%.

There remains a need in the art for an efficient, reliable and highly selective process for preparing chlorinated alkenes, such as 1,1,3-trichloropropene, which does not additionally result in the formation of unwanted impurities, especially those which are difficult to separate from the chlorinated alkene of interest and/or which can become problematic in downstream processes for example, by deactivating catalysts employed in those processes, and/or resulting in degradation or polymerisation of the haloalkene product.

Thus, according to a first aspect of the present invention, there is provided a process for preparing a chlorinated alkene comprising contacting a chlorinated alkane with a catalyst in a dehydrochlorination zone to produce a reaction mixture comprising the chlorinated alkane and the chlorinated alkene, and extracting the chlorinated alkene from the reaction mixture, wherein the concentration of the chlorinated alkene in the reaction mixture present in the dehydrochlorination zone is controlled such that the molar ratio of chlorinated alkene:chlorinated alkane is from 1:99 to 50:50.

It has unexpectedly been found that by controlling the level of chlorinated alkene such that the molar ratio of that product to the chlorinated alkane starting material does not exceed 50:50 advantageously prevents the formation of unwanted and problematic impurities, such as chlorinated oligomers which can adversely affect catalyst performance. Doing so also improves yield and catalyst activity. Advantageously, the processes of the present invention are also highly selective.

The molar ratio of chlorinated alkene:chlorinated alkane in the reaction mixture is controlled within numerically defined limits. As those skilled in the art will appreciate, in such embodiments, while control over the process is characterised herein in terms of the molar ratio between the chlorinated alkane starting material and the chlorinated alkene product, it can also considered as control over the conversion of starting material to product—thus a molar ratio of product:starting material of 20:80 equates to a conversion of 20%. The inventors have found that limiting the conversion of the starting material as outlined above minimises the formation of undesirable impurities and allows better catalyst lifetime. Additionally, where reference is made to a molar ratio of the product:starting material being greater than a given value, this means a greater degree of conversion of the starting material to product, i.e. such that the proportion of the product is increased while the proportion of the starting material is decreased. Moreover, the inventors have surprisingly found out that the required molar ratio between the chlorinated alkene product and the chlorinated alkane starting material in the reaction mixture can be controlled not only by significantly limiting the conversion of the starting alkane but, advantageously, also by efficient immediate extraction of produced alkene from such reaction mixture.

In embodiments of the invention the process is continuous.

The processes of the present invention result in the formation of chlorinated alkenes. As those skilled in the art will recognize, such compounds are typically highly reactive and the formation of oxygenated organic compounds, such as chlorinated alkanols, or chlorinated alkanoyl compounds in dehydrochlorination reactions of this type is possible. The importance of minimising such compounds in the products of the processes of the present invention has been recognised by the inventors of the present process. While the exclusion of air from the apparatus can reduce the formation of oxygenated compounds, doing so is typically more technically and economically demanding, especially where subatmospheric pressure environments are used.

The in situ formation of such side products can be prevented through use of processes of the present invention, and this is especially advantageous in continuous processes. The reaction conditions described herein enable the chlorinated alkene of interest to be produced selectively and be extracted from the reaction mixture, such that there is minimised risk of the production of undesired oxygenated compounds.

Additionally or alternatively, if oxygenated compounds are formed in the process of the present invention, e.g. alkanols or carbonyl compounds, then these can be removed through the use of an aqueous treatment step, discussed below in more detail.

Advantageous results have also been achieved when the chlorinated alkene content of the reaction mixture is controlled such that the molar ratio of chlorinated alkene product:chlorinated alkane starting material in the reaction mixture does not exceed 40:60, 30:70, 25:75, 20:80 or 15:85. Additionally or alternatively, in embodiments of the invention, the molar ratio of chlorinated alkene product:chlorinated alkane starting material in the reaction mixture may be equal to or greater than 2:98, 5:95 or 10:90.

Any technique or equipment may be used by those skilled in the art to determine the composition of the reaction mixture. For example, a direct determination of the composition can be made e.g. by providing the reaction zone with a port through which samples of the reaction mixture can be extracted for analysis and/or taking samples of reaction mixture upon extraction of that reaction mixture from the dehydrochlorination zone, e.g. via a port located at or in the vicinity of the outlet of the reaction zone. Additionally or alternatively, an indirect determination of the composition can be made e.g. by temperature control as temperature is a function of composition at constant pressure.

The level of chlorinated alkene in the reaction mixture may be controlled in one or more of the following ways: i) by removing the chlorinated alkene from the dehydrochlorination zone (either directly, or by firstly extracting reaction mixture from the dehydrochlorination zone and then extracting the chlorinated alkene therefrom), ii) control of the operating conditions in the dehydrochlorination zone (e.g. temperature, pressure, agitation speed, etc) which do not favour higher levels of chlorinated alkene formation, and/or iii) by controlling the amount of chlorinated alkane starting material and/or catalyst present in the dehydrochlorination zone.

Chlorinated alkene may be extracted from the reaction mixture on a continuous or batch-wise basis.

The chlorinated alkene may be extracted from the reaction mixture using any technique known to those in the art. In embodiments, the chlorinated alkene is extracted from the reaction mixture via distillation. Regardless of how extraction of the chlorinated alkene from the reaction mixture is carried out, the chlorinated alkene may be obtained as a stream rich in the chlorinated alkene.

As used throughout this specification, the term 'a stream rich in' a specific compound (or corresponding language) is used to mean that the stream comprises at least about 90%, about 95%, about 97%, about 98% or about 99% of the specific compound. Further, the term 'stream' should not be interpreted narrowly, but encompasses compositions (including fractions) extracted from a mixture via any means.

For the avoidance of doubt, where reference is made to 'continuous extraction' of the reaction mixture in the dehydrochlorination zone or to reaction mixture from the dehydrochlorination zone, a strict literal interpretation is not intended; one skilled in the art would recognise that the term is used to mean that extraction occurs on a substantially continuous basis, once the dehydrochlorination zone has attained the target operating conditions and the reaction mixture has attained a steady state.

The chlorinated alkene can be extracted directly from the reaction mixture in the dehydrochlorination zone (e.g. via direct distillation), or a portion of the reaction mixture can be firstly extracted from the dehydrochlorination zone (on a continuous or batchwise basis) and the chlorinated alkene extracted from that mixture, remotely from the dehydrochlorination zone.

In embodiments of the invention, the reaction mixture may be subjected to additional treatment steps, for example one or more distillation steps and/or aqueous treatment steps (discussed below in more detail). Such additional treatment steps may be carried out before and/or after extraction of chlorinated alkene from the reaction mixture. Those skilled in the art will recognise that where such additional treatment steps are conducted post-extraction of chlorinated alkene, the chlorinated alkene content of the mixture will be lower than that in the reaction mixture formed in the dehydrochlorination zone.

In embodiments of the invention, the chlorinated alkene may be removed from the reaction mixture by distillation. Any technique and apparatus known to those skilled in the art may be employed to effect extraction of the chlorinated alkene from the reaction mixture in this way. In embodiments of the invention, a distillation column may be used, for example a rectification column. The reaction mixture may pass or be fed into the column bottom, with the chlorinated alkene of interest being removed from the top of the column as a liquid distillate.

For example, in embodiments, in which the reaction mixture is totally or partially gaseous, for example due to the operating temperature in the dehydrochlorination zone, the apparatus may be configured such that the dehydrochlorination zone is in fluid communication with the apparatus for conducting the distillation. In such embodiments, the distillation apparatus may be coupled to the dehydrochlorination zone. Conveniently, this enables the gaseous chlorinated alkene-containing mixture to pass (or be passed) directly from the dehydrochlorination zone in to the distillation apparatus. Alternatively, the distillation apparatus may be located remotely from the dehydrochlorination zone, meaning that the gaseous mixture must be extracted from the dehydrochlorination zone and passed to the distillation apparatus.

Additionally or alternatively, where the reaction mixture is present in the dehydrochlorination zone either partly or totally in liquid form, a portion of the liquid reaction mixture may be extracted from the dehydrochlorination zone and passed to distillation apparatus. In such embodiments, the reaction mixture may be subjected to one or more treatment steps (e.g. an aqueous treatment step, discussed below) which may precede and/or follow distillation.

In embodiments where extraction of chlorinated alkene from the reaction mixture occurs in apparatus remote from the dehydrochlorination zone, the resulting mixture, comprising unreacted chlorinated alkane starting material and depleted levels of chlorinated alkene (if any) may be fed back into the dehydrochlorination zone.

In embodiments in which chlorinated alkene is extracted from the reaction mixture, at least about 30%, at least about 40%, at least about 50%, at least about 60%, at least about 70%, at least about 80%, or at least about 90% by weight of the chlorinated alkene present in the reaction mixture is extracted from that mixture.

Distillation of the chlorinated alkene from the reaction mixture can be carried out continuously, semi-continuously or batch-wise.

An advantage of the present invention is that the dehydrochlorination reaction produces highly pure gaseous hydrogen chloride from the chlorinated alkene mixture that may be recovered using routine techniques, for example by condensation of distillation apparatus overhead vapours.

Thus, in embodiments of the invention in which hydrogen chloride is produced during the dehydrochlorination reaction, the hydrogen chloride may be extracted. This can be achieved using any equipment and/or techniques for doing so known to those skilled in the art. For example, if the reaction mixture is subjected to distillation, the distillation apparatus may be provided with a condenser (e.g. a partial condenser), or a condenser (e.g. a partial condenser) may be provided downstream of the distillation apparatus, to enable the removal of hydrogen chloride gas.

Cooling apparatus (e.g. a second condenser) may additionally be employed, e.g. downstream of the first condenser. Arranging the apparatus in this way is advantageous as the first condenser can be used to condense the bulk of the chlorinated alkene, with the second condenser being used to purify the gas by condensing traces of the chlorinated alkene. The recovered chlorinated alkene is highly pure as is the hydrogen chloride.

Additionally or alternatively, an absorption column may be employed to absorb hydrogen chloride gas to produce hydrochloric acid solution.

In embodiments of the present invention, in which hydrogen chloride gas is extracted from the dehydrochlorination zone or from reaction mixture extracted therefrom, this may be achieved through the use of deep cooling, i.e. by extracting the gas from the reaction mixture and then cooling it to a temperature of about 0° C. or lower, about −10° C. or lower or about −20° C. or lower. The resulting condensate may be recycled back to the dehydrochlorination zone or optionally used in other associated reaction zones, e.g. hydrochlorination of glycerol.

Advantageously, hydrogen chloride extracted in these ways is highly pure and thus can be used as a reactant in upstream or downstream reactions in the same industrial plant. An example of downstream use is for the hydrochlorination of glycerol to make monochlorohydrin or dichlorohydrin, and subsequently to lead to epichlorohydrin, glycidol and epoxies.

As mentioned above, the rate of the reaction (and thus the molar ratio of chlorinated alkane:chlorinated alkene) can be controlled by modification of the operating temperature in the dehydrochlorination zone. In embodiments of the invention, the dehydrochlorination reaction is carried out in the liquid phase, i.e. the reaction mixture is in the liquid form. In such embodiments, the dehydrochlorination zone may be operated at a temperature of about 50° C., about 60° C., about 70° C., about 80° C., about 100° C., about 120° C. or about 130° C. to about 160° C., about 170° C., about 200° C., about 250° C. or about 300° C.

The reaction mixture is maintained in the dehydrochlorination zone for a period sufficient to enable the reaction (the conversion of chlorinated alkane to chlorinated alkene) to proceed to the required degree of completion. In embodiments of the invention, in which dehydrochlorination occurs in the liquid phase, the residence time of the reaction mixture in the dehydrochlorination zone may range from about 0.1, about 0.2, about 0.5, about 1, about 1.5, about 2, about 2.5 or about 3 to about 5 hours, about 7 hours, about 9 hours or about 10 hours.

The dehydrochlorination zone may be operated at subatmospheric pressure, atmospheric pressure or superatmospheric pressure. In embodiments of the invention, the dehydrochlorination zone is operated at atmospheric pressure or a pressure of about 10 kPa to about 400 kPa, about 40 kPa to about 200 kPa, or about 70 kPa to about 150 kPa.

Any catalyst which increases the rate of the dehydrochlorination reaction may be employed in the processes of the present invention. In embodiments, the catalyst comprises a metal. In such embodiments, the metal may be present in solid form (e.g. where the catalyst is iron, it may be present as particulate iron (e.g. iron filings or iron powder) iron mesh, iron wire, packing (structured or random), fixed bed, fluid bed, dispersions in liquid, etc. or in alloys containing iron formed in any such way, e.g. carbon steel), and/or as a salt (e.g. where the catalyst is iron, it may be present as ferric chloride, ferrous chloride, etc). Additionally or alternatively, the apparatus in which the process of the present invention is conducted may be provided with components formed either partially or totally of catalyst material, for example column internals.

In embodiments of the invention in which metal is present in the reaction mixture as a salt, it may be added to the reaction mixture in salt form and/or solid metal may be added to the reaction mixture, which then dissolves in the reaction mixture, forming the salt in situ. When present in the form of a salt, the catalyst may be added in amorphous form, crystalline form, anhydrous form and/or in hydrated form (e.g. ferric chloride hexahydrate). Liquid form catalysts may also be employed.

In alternative embodiments, the dehydrochlorination reaction is carried out in the vapour phase, i.e. both the chlorinated alkane and the chlorinated alkene are in gaseous form. In such embodiments, the dehydrochlorination zone may be operated at a temperature of about 300° C. to about 500° C., about 325° to about 425° C. or about 350° C. to about 400° C.

In embodiments of the invention in which the dehydrochlorination reaction occurs in the vapour phase, the residence time of the reaction mixture in the dehydrochlorination zone may range from about 0.5 to about 10 seconds.

It has been surprisingly found that, in embodiments of the invention in which the dehydrochlorination reaction is carried out in the vapour phase, the reaction must be properly catalysed in order to attain high yield and selectivity. Therefore, in processes of the invention, a metallic catalyst may be used, for example one containing iron at levels of 50% by weight or greater.

Thus, according to a further aspect of the present invention, there is provided a process for preparing a chlorinated alkene comprising contacting a chlorinated alkane in the vapour phase with a catalyst having an iron content of 50% or greater in a dehydrochlorination zone to produce a vapour-phase reaction mixture comprising the chlorinated alkane and the chlorinated alkene.

Examples of catalysts which may be employed in processes of the present invention include stainless steels, for example ferritic and/or austenic steels. Catalysts employed in processes of the present invention preferably have an iron content of at least about 50%, at least about 60%, at least about 70%, at least about 80%, at least about 90% or at least about 95% by weight. Pure iron may be employed as a catalyst.

Catalysts may be employed in any form, for example fluid bed arrangements and/or fixed bed arrangements. Additionally or alternatively, components of the dehydrochlorination zone comprising the catalyst can be employed. For example, in embodiments in which the dehydrochlorination zone is in a tube reactor, the reactor tubes (or at least the surfaces of those tubes in contact with the chlorinated alkane) can be formed (partially or completely) of the catalyst, or be provided with catalytic zones formed of the catalyst.

During operation of the dehydrochlorination reaction in the vapour phase of the present invention, the catalyst may become deactivated. Thus, in such embodiments, the processes of the present invention include a catalyst recovery step. This step can be achieved using any techniques and/or equipment known to those skilled in the art, for example, by the injection of an oxidant such as oxygen-rich air and/or oxygen into the dehydrochlorination zone. Prior to such a step, the flow of reactants through the dehydrochlorination zone may be stopped and/or the dehydrochlorination zone may be purged (for example with nitrogen gas). If performed, once the catalyst recovery step is completed, the dehydrochlorination zone may again be purged (for example with nitrogen gas) and/or the flow of reactants into the dehydrochlorination zone can be re-started.

In embodiments in which the dehydrochlorination step is conducted in the vapour-phase, the reaction mixture extracted from the dehydrochlorination zone is typically in the vapour phase. Those hot product gases may be condensed using any technique and/or equipment known to those skilled in the art, to obtain chlorinated organic compounds in liquid form. For example, the hot reaction mixture can be cooled by indirect cooling methods, quenching (for example using spray nozzles), direct cooling methods, or the like.

Upon cooling the gases to condense the chlorinated organic compounds from the reaction mixture, hydrogen chloride gas may be extracted which can optionally be used in upstream or downstream processes. An example of downstream use is for the hydrochlorination of glycerol to make monochlorohydrin or dichlorohydrin, and subsequently to lead to epichlorohydrin and epoxies.

Regardless of whether the dehydrochlorination step occurs in the gaseous or liquid phase, the mixture of chlorinated organics, including the chlorinated alkene of interest and unreacted chlorinated alkane, as well as impurities may then be subjected to one or more post dehydrochlorination treatment steps as discussed herein (including one or more distillation and/or aqueous treatment steps) to obtain pure chlorinated alkene, e.g. 1,1,3-trichloropropene.

Any type of reactor known to those skilled in the art may be employed in the processes of the present invention. Specific examples of reactors that may be used to provide a dehydrochlorination zone are column reactors, tubular reactors, bubble column reactors, plug/flow reactors and continuously stirred tank reactors.

The process of the present invention may be carried out in a single dehydrochlorination zone or in a plurality of dehydrochlorination zones. Where a plurality of dehydrochlorination zones are employed, these may be operated in sequence (i.e. such that reaction mixture is passed along a number of dehydrochlorination zones) and/or in parallel.

In embodiments of the invention, where a plurality of dehydrochlorination zones are employed optionally in cascade mode, these may be in the same or different reactors. For example, where a plurality of (e.g. 1, 2, 3, 4, 5 or more) dehydrochlorination zones are employed, these may be provided in a plurality (e.g. 1, 2, 3, 4, 5 or more) of reactors (e.g. continuously stirred tank reactors) which may each be optimised to have optimised operating conditions such as temperature, residence times, In an embodiment, a plurality of dehydrochlorination zones may be present in a distillation column that may be employed in processes of the present invention. In such embodiments, dehydrochlorination may be achieved by reactive distillation, for example where the dehydrochlorination reaction is carried out on trays in a distillation column and/or on packing provided in the column. In embodiments in which reactive distillation is carried out, the distillation column preferably comprises a stripping zone in alkene is separated from alkane. The stripping zone may be located below the liquid feed.

It has been found that the components of the reaction mixture (e.g. chlorinated alkene, hydrogen chloride and/or the starting material) obtainable from the dehydrochlorination reaction which is conducted in the processes of the present invention, can unfavourably interact with certain materials. Thus, in embodiments of the invention, those parts of the dehydrochlorination zone which are in contact with the reaction mixture may have an iron content of about 20% or less, about 10% or less or about 5% or less, and/or are formed from non-metallic materials, for example enamel, glass, impregnated graphite (e.g. impregnated with phenolic resin), silicium carbide and/or plastics materials such as polytetrafluoroethylene, perfluoroalkoxy and/or polyvinylidene fluoride.

In embodiments of the invention, the surfaces of all equipment employed in the processes of the present invention with which chlorinated alkene will contact are formed from suitable materials such as those identified above. One possible exception is where one or more regions of the surfaces of the apparatus employed in the processes of the present invention are formed of metallic material which is selected to perform as a catalyst.

The inventors have also found that, under certain operating conditions, the exposure of the reactants used in the processes of the present invention as well as the compounds formed in those processes to sources of oxygen and/or moisture, including air, water vapour and/or water can lead to the formation of unwanted impurities. Thus, in embodiments of the present invention, dehydrochlorination and/or distillation may be conducted in an inert atmosphere, e.g. in the absence of oxygen.

The chlorinated alkane employed in the processes of the present invention may be fed into the dehydrochlorination zone using any technique known to those skilled in the art. The chlorinated alkane may be a $C_{2-6}$ alkane, for example, chloroethane, chloropropane or chlorobutane. An example of a chlorinated alkane which may be employed in the processes of the present invention is 1,1,1,3-tetrachloropropane, 1,1,2,2,-tetrachloropropane, 1,1,2,3-tetrachloropropane, 1,2,2,3-tetrachloropropane, 1,1,1,2-tetrachloropropane, 1,1,2-trichloropropane, 1,2,2-trichloropropane, 1,2,3-trichloropropane, 1,1,1,2,3-pentachloropropane, 1,1,2,3,3-pentachloropropane, 1,1,1,2,2-pentachloropropane, 1,1,2,2,3-pentachloropropane, 1,1,1,3,3-pentachloropropane, or any chlorinated alkane having the formula: $CX_3$—R or $CX_aY_b$—R, where a=0-3, b=0-3, X and Y are the same or different halogen (e.g. chlorine, fluorine, bromine, iodine) and R is a substituted or unsubstituted $C_{2-5}$ alkyl.

The chlorinated alkane used as a starting material in the processes of the present invention preferably has a high degree of purity.

In embodiments of the invention, the chlorinated alkane has a purity level of at least about 95%, at least about 97%, at least about 98%, at least about 98.5%, at least about 99%, or at least about 99.5%.

In embodiments, the chlorinated alkane contains less than or equal to about 1000 ppm, less than or equal to about 500 ppm, less than or equal to 250 ppm or less than or equal to about 100 ppm of chlorinated alkane impurities, for example alkanes having a boiling point which is equal to or greater than the boiling point of the chlorinated alkane starting material and/or the chlorinated alkene of interest and/or which, in the reaction conditions are dehydrochlorinated to produce a chlorinated alkene impurity, for example alkenes which have a boiling point within 10° C. of the alkene of interest, which have a boiling point equal to or greater than the chlorinated alkane starting material, and/or which are isomers of the chlorinated alkene of interest.

In additional or alternative embodiments, the chlorinated alkane contains less than or equal to about 1000 ppm, less than or equal to about 500 ppm, less than or equal to 250 ppm or less than or equal to about 100 ppm of chlorinated alkene impurities, for example alkenes which have a boiling point within 10° C. of the alkene of interest, which have a boiling point equal to or greater than the chlorinated alkane starting material, or the chlorinated alkene compound of interest, and/or which are isomers of the chlorinated alkene of interest.

Additionally or alternatively, the chlorinated alkane comprises less than or equal to about 1000 ppm, less than or equal to about 500 ppm, less than or equal to about 200 ppm, less than or equal to about 100 ppm, less than or equal to about 50 ppm, less than or equal to about 20 ppm or less than or equal to about 10 ppm of tetrachloroethene, tetrachloropropane and/or tetrachloropentane.

Processes for producing high purity chlorinated alkane are disclosed in UK Patent Application No. 1418346.1 and Czech Patent Application No. PV 2014-705, the contents of which are hereby incorporated by reference. Products of those processes advantageously comprise:

less than about 2000 ppm, less than about 1000 ppm, less than about 500 ppm, less than about 200 ppm or less than about 100 ppm chlorinated alkane impurities (i.e. chlorinated alkane compounds other than the chlorinated alkane starting material), less than about 2000 ppm, less than about 1000 ppm, less than about 500 ppm, less than about 200 ppm or less than about 100 ppm chlorinated alkene impurities (i.e. chlorinated alkene compounds other than the chlorinated alkene target compound), less than about 1000 ppm, less than about 500 ppm, less than about 200 ppm, less than about 100 ppm, less than about 50 ppm or less than about 20 ppm of water, less than about 2000 ppm, less than about 1000 ppm, less than about 500 ppm, less than about 200 ppm or less than about 100 ppm oxygenated organic compounds, less than about 2000 ppm, less than about 1000 ppm, less than about 500 ppm, less than about 200 ppm or less than about 100 ppm brominated compounds, and/or less than about 500 ppm, less than about 200 ppm, less than about 100 ppm, less than about 50 ppm or less than about 20 ppm metal.

The chlorinated alkane material used as a starting material in the processes of the present invention may be provided in a composition having the impurity profile as outlined above.

The inventors of the process disclosed herein have found that, in embodiments of the present invention, certain impurities, such as hexachloroethane and/or higher alkanes, e.g. chloropentanes, such as tetrachloropentane, e.g. 1,3,3,5-tetrachloropentane (when the chlorinated alkane starting material is 1,1,1,3-tetrachloropropane) which may be present in industrial scale supply volumes of chlorinated alkanes (e.g. 1,1,1,3-tetrachloropropane), can severely retard the dehydrochlorination reaction process.

Thus, in such embodiments, higher purity starting haloalkanes, with reduced amounts of such higher haloalkane impurities may be preferable such that efficient conversion to the desired haloalkene is achieved at lower temperatures.

The chlorinated alkene produced in the processes of the invention may be a $C_{2-6}$ alkene, for example, chloroethene, chloropropene or chlorobutene. An example of a chlorinated alkene which may be produced in the processes of the invention is 1,1,3-trichloropropene (1240za), 1,1,3,3-tetrachloropropene (1230za), 1,1,2,3-tetrachloropropene (1230xa), 2,2,2,3-tetrachloropropene (1230xf), 3,3,3-trichloropropene, 2,3,3,3-tetrachloropropene and chlorinated alkenes having the formula: $CX_cY_d$=R, where X and Y are the same or different halogen (e.g. fluorine or chlorine), c is 0 to 2, d is 0 to 2 and R is a substituted or unsubstituted $C_{2-5}$ alkyl.

One of the advantages of the processes of the present invention is that they permit the production of a target chlorinated alkene with high isomeric selectivity. Thus, in embodiments of the invention, the chlorinated alkene product is produced with isomeric selectivity of at least about 95%, at least about 97%, at least about 98%, at least about 99%, at least about 99.5%, at least about 99.7%, at least about 99.8% or at least about 99.9%.

The feed of chlorinated alkane and/or catalyst into the dehydrochlorination zone may be continuous or intermittent, as may extraction of the reaction mixture.

One advantage of the processes of the present invention is that desirous results are obtained whether the dehydrochlorination zone is operated in a continuous or batch process. The terms 'continuous process' and 'batch process' will be understood by those skilled in the art.

A further advantage of the present invention is that it enables high purity chlorinated alkene compounds to be produced without the use of alkaline hydroxides. Thus, in embodiments or the present invention, no alkaline hydroxide is added to the dehydrochlorination zone and/or the reaction medium present in the dehydrochlorination zone is free of alkaline hydroxide.

As mentioned above, in embodiments of the invention, reaction mixture comprising chlorinated alkane, chlorinated alkene and catalyst may be extracted from the dehydrochlorination zone. This may be subjected to further treatment steps.

In such embodiments, such a treatment step may be an aqueous washing step in which the extracted mixture is optionally filtered and then fed into an aqueous treatment zone. This step may be carried out before or after extraction of the chlorinated alkene from the mixture.

The mixture is contacted with an aqueous medium in the aqueous treatment zone which serves to deactivate the catalyst. The mixture may be contacted with acid in the aqueous treatment zone, for example inorganic acid such as sulphuric acid, phosphoric acid and/or hydrochloric acid. The acid may be pure, or may be dilute. Where dilute acid is used, this may provide the aqueous medium. The pH value of the aqueous medium should be sufficiently low to enable effective separation of the biphasic mixture.

The aqueous treatment step has the advantageous effect of removing certain classes of otherwise problematic impurities from the mixture, especially oxygenated impurities.

In such embodiments, catalyst deactivation can be achieved with only a short contact time, e.g. about 5, about 10, about 20 or about 30 minutes, with water at low temperature is required. For hydrolysis and extraction of chlorinated, oxygenated impurities, the contact time with the water may be longer, e.g. up to about 1 hour, about 2 hours, about 5 hours or about 10 hours and/or at a temperature of about 50° C. or less, about 40° C. or less or about 30° C. or less.

Thus, according to a further aspect, there is provided a process for removing oxygenated organic impurities from a mixture comprising a chlorinated alkene, oxygenated organic impurities and optionally a catalyst and/or a chlorinated alkane, comprising contacting the mixture with an aqueous medium to form a biphasic mixture and extracting the organic phase from that biphasic mixture. In embodiments of the invention, the mixture of this aspect of the invention is or comprises the mixture extracted from the dehydrochlorination zone.

Where a dilute acid is employed, this may additionally provide the aqueous medium with which the mixture is contacted. Additionally, or alternatively, the aqueous medium may comprise water (in any form, e.g. including steam) which may be added separately into the aqueous treatment zone.

In embodiments in which acid is added into the aqueous treatment zone, this preferably reduces the pH of the mixture present therein to about 6 or lower, about 5 or lower, about 4 or lower, about 2 or lower or about 1 or lower.

A proportion (e.g. at least about 30%, at least about 40%, at least about 50%, at least about 60%, at least about 70%, or at least about 80%) of the unreacted alkane and/or chlorinated alkene may be extracted from the mixture formed in the aqueous treatment zone using any techniques or equipment known to those skilled in the art.

For example, in embodiments in which the mixture is partly or totally in gaseous form, for example due to the operating temperature in the aqueous treatment zone and/or through the addition of steam as the aqueous medium, the gaseous mixture may be subjected to distillation. In such embodiments, the distillation device may be in fluid communication with the aqueous treatment zone (optionally coupled to that zone) or may be remote from the aqueous treatment zone.

Additionally or alternatively, where the mixture is partly or totally in liquid form, that mixture may be extracted from the aqueous treatment zone and subjected to distillation.

In embodiments where such a distillation step is conducted, a stream comprising (and optionally rich in) chlorinated alkane starting material and/or chlorinated alkene product may be obtained.

The chlorinated alkane and/or chlorinated alkene extracted from the mixture fed in to the aqueous treatment zone may be recycled back to the dehydrochlorination zone for use as a starting material.

A biphasic mixture, comprising an aqueous phase and an organic phase may be formed in the aqueous treatment zone (or in certain embodiments, remotely therefrom), as a result of the presence of both the aqueous medium and also the predominantly organic mixture.

In such embodiments where a biphasic mixture is formed, the organic phase may be extracted from the biphasic mixture using phase separation techniques and/or equipment known to those skilled in the art. Where the biphasic mixture is formed in the aqueous treatment zone, the organic phase can be separated from the aqueous phase by the sequential extraction of the phases from the aqueous treatment zone. The aqueous phase, which contains impurities removed from the mixture can be further treated.

To maximise phase separation efficiency and thus facilitate extraction of that phase from the biphasic mixture, a haloalkane extraction agent and/or phase separation intensifier (for example, the chlorinated alkane starting material and/or various alcohols and/or ketones) may be added to the aqueous treatment zone, either intermittently or continuously, using techniques and/or equipment known to those skilled in the art. The use of the chlorinated alkane starting material is preferred as this compound is part of the process and thus does not require removal using specific separation steps.

Optionally, phase separation intensifiers such as polar alcohols and/or ketones with boiling points sufficiently different to the chlorinated alkene and chlorinated alkane present in the reaction mixture may be employed. The difference in boiling points should be at least 20° C., at least about 30° C., at least about 40° C., at least about 50° C. or at least about 60° C. Examples of phase separation intensifiers that may be employed include aliphatic ketones e.g. acetone and aliphatic alcohols e.g. methanol, ethanol, propanol/s, butanol/s.

In embodiments of the invention, the extracted organic phase may then be subjected to a distillation step in which streams of (and optionally rich in) the chlorinated alkene of interest and/or unreacted chlorinated alkane are distilled off. Such a step may be performed regardless of whether extraction of chlorinated alkene from the reaction mixture was carried out prior to aqueous treatment or not. The stream of unreacted chlorinated alkane may be recycled back to the dehydrochlorination zone. A heavy ends residue may be extracted from the distillation apparatus, optionally filtered and incinerated and/or subjected to high temperature chlorinolysis.

The organic phase comprising chlorinated alkane and/or chlorinated alkene as well as haloalkane extraction agent and/or phase separation intensifier may be fed back in to the dehydrochlorination zone. In such embodiments, a distillation step to remove the phase separation intensifier (if used) or other components of the organic phase may be conducted.

Reducing the water content of chlorinated alkene has been found to use such alkene in downstream applications such as chlorination. Thus, in embodiments of present invention, process conditions are controlled such that the obtained chlorinated alkene product/s comprise less than about 500 ppm, about 250 ppm or less, about 100 ppm or less or about 50 ppm or less of water.

As can be seen from the disclosure provided herein, the inventive processes of the present invention can be operated in an integrated process in a fully continuous mode, optionally in combination with other processes. The process steps of the present invention may employ starting compounds which are converted to highly pure intermediates which are themselves further processed to the required target chlorinated compounds. Those compounds have the requisite purity to be employed as feedstocks in a range of downstream processes, for example hydrofluorination conversions.

The processes of the present invention enable product purity levels to be controlled to attain highly pure target compounds. The processes advantageously balance high yields, high selectivity and high efficiency which is particularly challenging, especially in continuous processes. The processes of the present invention enable high purity chlorinated alkene compounds to be economically produced on an industrial scale, those compounds having very low levels of a range of impurities, The processes of the present invention are particularly advantageous as they enable highly pure chlorinated alkenes to be produced using simple and straightforward techniques and equipment with which one skilled in the art would be familiar.

In embodiments of the invention, the processes of the invention can be used to produce high purity chlorinated alkene compositions which comprise:

About 95% or more, about 97% or more, about 99% or more, about 99.2% or more about 99.5% or more or about 99.7% or more of the chlorinated alkene, Less than about 50000 ppm, less than about 20000 ppm, less than about 10000 ppm, less than about 5000 ppm, less than about 2000 ppm, less than about 1000 ppm, less than about 500 ppm, less than about 200 ppm, or less than about 100 ppm of chlorinated alkane starting material, Less than about 1000 ppm, less than about 500 ppm, less than about 200 ppm, or less than about 100 ppm of chlorinated $C_{5-6}$ alkane impurities, Less than about 1000 ppm, less than about 500 ppm, less than about 200 ppm, or less than about 100 ppm of chlorinated alkene impurities (i.e. chlorinated alkenes other than the compound of interest), Less than about 500 ppm, less than about 200 ppm, less than about 100 ppm, less than about 50 ppm, less than about 20 ppm, less than about 10 ppm or less than about 5 ppm metal, Less than about 1000 ppm, less than about 500 ppm, less than about 250 ppm, or less than about 100 ppm of oxygenated organic compounds and/or Less than about 500 ppm, about 250 ppm or less, about 100 ppm or less or about 50 ppm or less of water.

In embodiments of the invention, stabilisers can be added to the compositions of the present invention. Examples of stabilisers that may be employed include hydroxylated aromatic compounds, amines, thiazines, etc. Where employed, stabilisers are typically employed in amounts of about 1 to about 100 ppm or about 2 to about 50 ppm. The use of such stabilisers advantageously enables the chlorinated alkene compositions of the present invention to be stored in oxygen-containing environments.

As mentioned previously, the prior art fails to disclose or teach processes for producing chlorinated alkenes having such a high degree of purity or high isomeric selectivity. Thus, according to further aspects of the present invention, there are provided high purity chlorinated alkene compositions as set out above.

The impurity profile of compositions comprising chlorinated alkenes of the present invention can be determined using conventional analytical methods including gas chromatography using a high performance capillary column.

For the avoidance of doubt, where reference is made to units of pressure (kPa) it is the absolute value which is identified. Where values are presented as percentages, they are percentages by weight unless otherwise stated.

| | |
|---|---|
| 1 | 1,1,1,3-tetrachloropropane feed stream |
| 2 | ferric chloride feed stream |
| 3 | continuously stirred tank reactor |
| 4 | reaction residue |
| 5 | filter |
| 6 | filter cake |
| 7 | filtrate |
| 8 | distillation column |
| 9 | 1,1,3-trichloropropene rich stream |
| 10 | partial condenser |
| 11 | gaseous hydrogen chloride stream |
| 12 | 1,1,3-trichloropropene rich stream |
| 13 | reflux divider |
| 14 | reflux stream |
| 15 | purified 1,1,3-trichloropropene product stream |

Figure 2:
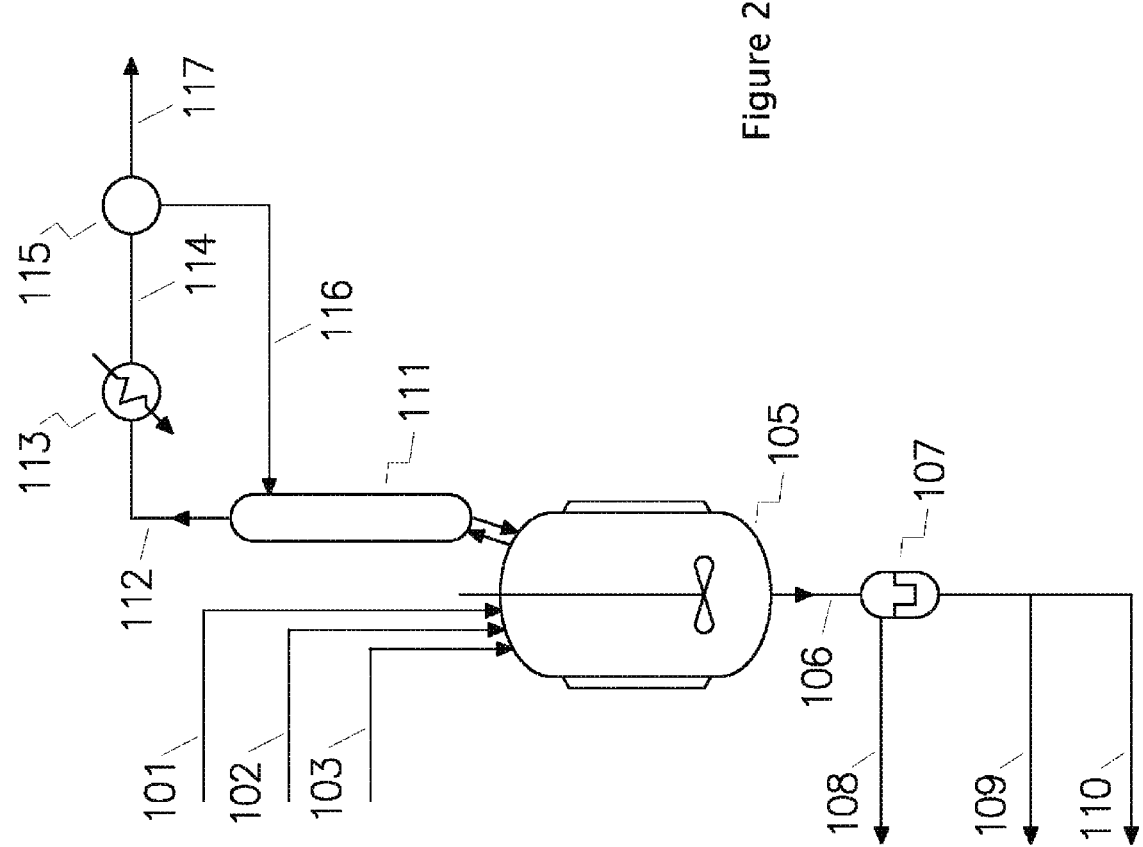

FIG. 2—Aqueous treatment step

| | |
|---|---|
| 101 | aqueous hydrochloric acid feed stream |
| 102 | residue feed stream (from the reactor in FIG. 1, stream 4) |
| 103 | haloalkane extraction agent feed stream |
| 104 | |

-continued

| 105 | washing tank |
| 106 | washing tank outlet |
| 107 | filter |
| 108 | filter cake |
| 109 | organic phase stream |
| 110 | aqueous phase stream |
| 111 | distillation column |
| 112 | chlorinated alkanes stream |
| 113 | condenser |
| 114 | intermediate line |
| 115 | reflux liquid-liquid separator |
| 116 | aqueous phase (reflux) stream |
| 117 | organic phase (1,1,1,3-tetrachloropropane) stream |

Figure 3:
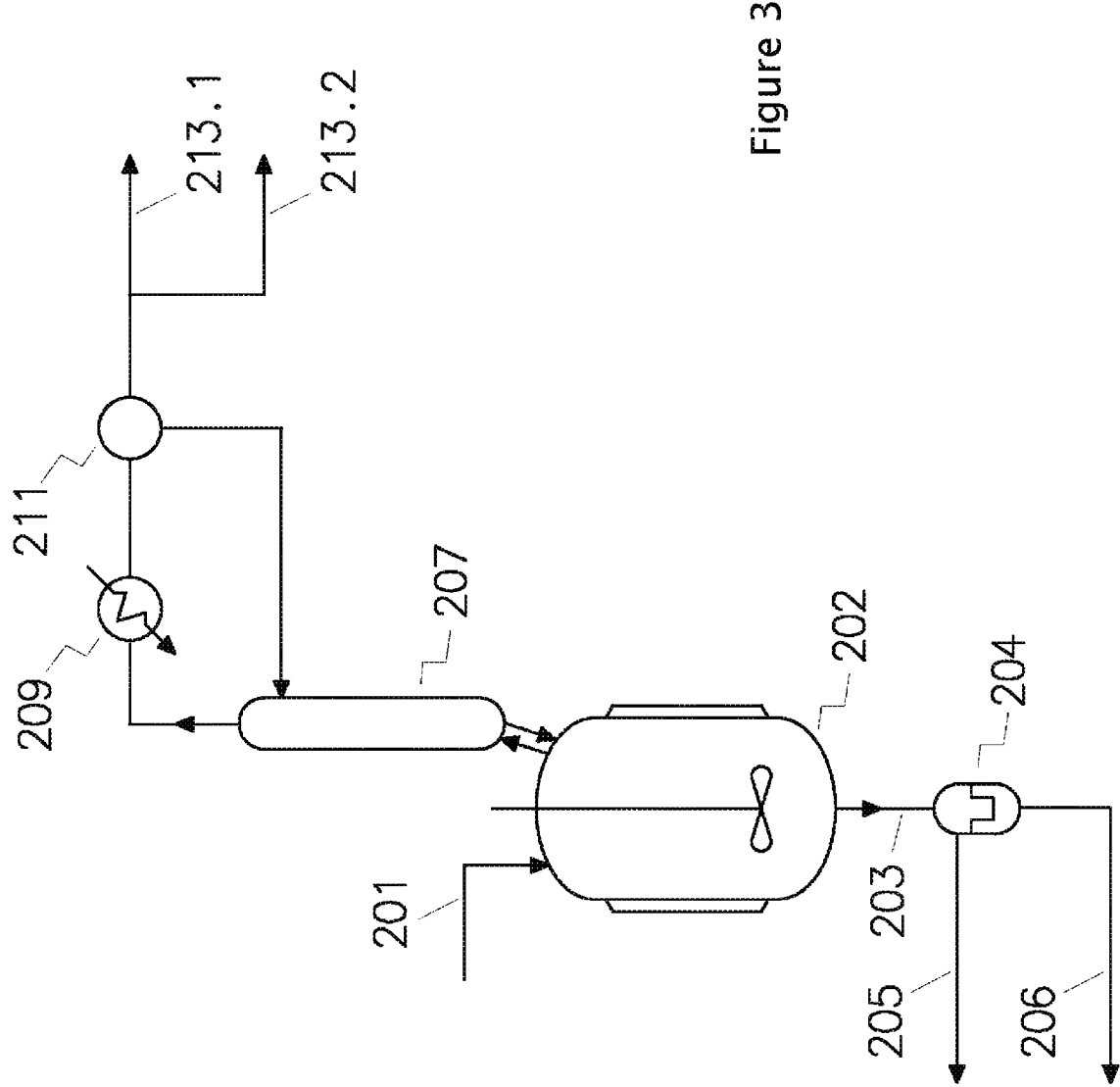

FIG. 3—Distillation step

| 201 | organic phase feed stream |
| 202 | distillation boiler |
| 203 | heavy ends residue stream |
| 204 | filter |
| 205 | filter cake |
| 206 | liquid residue |
| 207 | distillation column |
| 208 | distillate stream |
| 209 | condenser |
| 210 | intermediate line |
| 211 | reflux divider |
| 212 | reflux stream |
| 213.1 | 1,1,3-trichloropropene fraction |
| 213.2 | 1,1,1,3-tetrachloropropane fraction |

EXAMPLES

Abbreviations used:
TeCPa=1,1,1,3-tetrachloropropane
TCPe=trichloropropene

Example 1

Production of 1,1,3-Trichloropropene from 1,1,1,3-Tetrachloropropane

Figure 1:
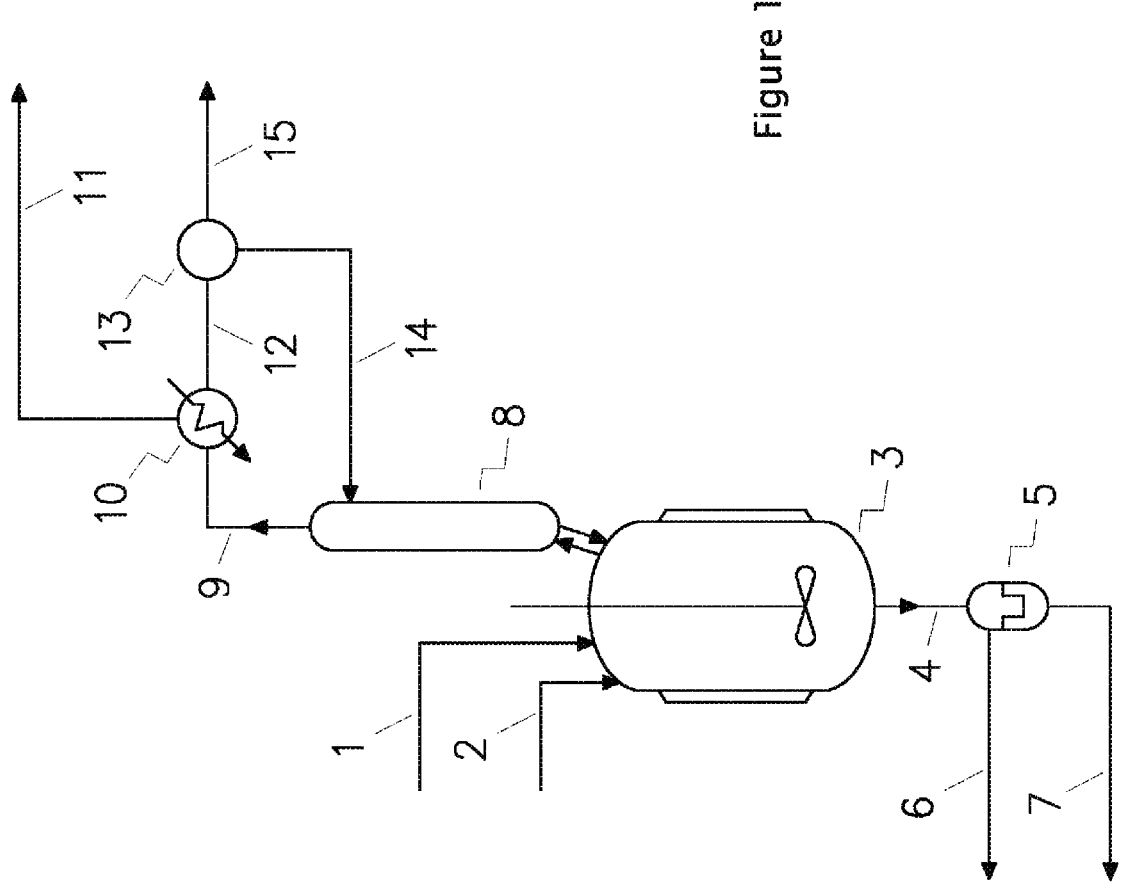
FIG. 1—Dehydrochlorination step (1,1,1,3-tetrachloropropane conversion to 1,1,3-trichloropropene)

FIG. 1 shows a schematic drawing of a system which can be used to operate processes of the present invention. 1,1,1,3-tetrachloropropane and ferric chloride are added into the continuously stirred tank reactor 3 via lines 1 and 2. The addition of ferric chloride is conducted using a controlled feed. The continuously stirred tank reactor is operated at a temperature of 140° C. to 145° C. and at atmospheric pressure.

The 1,1,1,3-tetrachloropropane is converted to 1,1,3-trichloropropene in the continuously stirred tank reactor 3, which fulfils the role of the dehydrochlorination zone. The residence time of the reaction mixture in the reactor 3 is limited to prevent the excessive conversion of 1,1,1,3-tetrachloropropane to 1,1,3-trichloropropene and thus, the molar ratio of 1,1,3-trichloropropene:1,1,1,3-tetrachloropropane does not exceed 50:50.

A proportion of 1,1,3-trichloropropene is extracted from the reaction mixture through the use of distillation column 8. Reaction mixture is fed into the bottom of the distillation column 8 and a 1,1,3-trichloropropene rich stream is withdrawn as overhead vapours via line 9. A partial condenser 10 functions to extract gaseous hydrogen chloride from the 1,1,3-trichloropropene rich stream via line 11. The 1,1,3-trichloropropene rich stream is then fed via line 12 to a reflux divider 13, and a stream of purified 1,1,3-trichloropropene is taken off via line 15. A proportion of the 1,1,3-trichloropropene rich stream is fed back as a reflux to distillation column 8 via line 14.

A mixture comprising catalyst, unreacted 1,1,1,3-tetrachloropropane and a limited amount of 1,1,3-trichloropropene is extracted via line 4 from the reactor 3 to a filter 5. The obtained filter cake is extracted via line 6 and the filtrate is passed via line 7 for aqueous treatment, as shown in FIG. 2.

In FIG. 2, the mixture from the reactor in FIG. 1 is fed via line 102 into a washing tank 105 including a stripping boiler. For better liquid phase separation efficiency, 1,1,1,3 tetrachloropropane or another haloalkane extraction agent is fed into the washing tank via line 103. Aqueous hydrochloric acid is fed into the washing tank 105 via line 101.

A biphasic mixture is formed in the tank 105 and the organic phase is extracted from the tank 105 via line 106, filtered 107 and taken via line 109 for further treatment, as shown in FIG. 3. The remaining aqueous phase is extracted via line 110 for further treatment. The filter cake is extracted (108)

1,1,1,3-tetrachloropropane and 1,1,3-trichloropropene dissolved in the aqueous layer present in the washing tank 105 are extracted therefrom by means of a steam distillation column 111. Stripped chlorinated alkanes are passed via line 112 from the distillation column 111 to a condenser 113 and then via line 114 to a reflux liquid-liquid separator 115 where two layers are formed. The stripped 1,1,1,3-tetrachloropropane is then taken off as an organic phase via line 117 and an aqueous phase is refluxed back to the distillation column via line 116.

Turning to FIG. 3, the organic phase is fed via line 201 into distillation boiler 202. 1,1,1,3-tetrachloropropane and 1,1,3-trichloropropene are extracted from the formed mixture using distillation column 207, condenser 209 and reflux divider 211 to produce fractions of 1,1,3-trichloropropene 213.1 and 1,1,1,3-tetrachloropropane 213.2. The fraction of 1,1,1,3-tetrachloropropane is recycled back to the dehydrochlorination zone while the fraction of 1,1,3-trichloropropene is stored or transported for use in downstream reactions employing that chlorinated alkene as a starting material A heavy ends residue is extracted from boiler 202 via line 203 and filtered 204. The obtained filter cake and liquid residue are extracted via lines 205 and 206 respectively and recycled or treated.

Using the apparatus and process conditions outlined above, 3563 kg of 1,1,1,3-Tetrachloropropane (1113TeCPa, 99.925% purity) was continuously processed with an average hourly loading 63.1 kg/h to produce 1,1,3-Trichloropropene (113TCPe). Basic parameters of disclosed process carried out according to Example 1 are as following.

| Basic parameters | |
| --- | --- |
| Reactor mean residence time (min) | 174 |
| Reactor temperature (° C.) | 141 |
| Reactor pressure (kPa) | 101 |
| Overall reaction 1113TeCPa conversion (%) | 91.7 |
| Overall 113TCpe reaction yield (mol TCPe/mol TeCPa converted, in %) | 97.4 |
| Overall 113TCpe yield including the all process steps described in Example 1 | 96.5 |

The full impurity profile of the purified product of the above-described embodiment is presented in the following table. The figures are given as a weighted average of the profiles for the product obtained in line 15 in FIG. 1 and line 213.1 in FIG. 3.

| Pilot plant | Wt % |
|---|---|
| Perchloroethylene | 0.011 |
| 1,1,3-Trichloropropene | 97.093 |
| 2,3-dichloropropanoyl chloride | 0.028 |
| 1,1,3,3-Tetrachloropropene | 0.019 |
| 1,1,1,3-Tetrachloropropane | 2.573 |
| unknown | 0.276 |

As can be seen, the process of the present invention can be operated to produce highly pure chlorinated alkene material.

Example 2

Production of 1,1,3-Trichloropropane from 1,1,1,3-Tetrachloropropane

This example was conducted using the apparatus and techniques employed in Example 1 above, except where otherwise stated. The continuously stirred tank reactor was operated at a temperature of about 149° C. and at atmospheric pressure. The molar ratio of 1,1,3-trichloropropene: 1,1,1,3-tetrachloropropane in the reactor was controlled such that it did not exceed 30:70. Using the apparatus and process conditions outlined above, 1543.8 kg of 1,1,1,3-Tetrachloropropane (1113TeCPa, 99.901% purity) was continuously processed with an average hourly loading 47.5 kg/h to produce 1,1,3-Trichloropropene (113TCPe). Catalyst was added in the form of FeCl$_3$ aqueous solution to provide a catalyst content of 66 ppm, based on feedstock 1113TeCPa. Basic parameters of disclosed process carried out according to Example 1 are as following.

| Basic parameters | |
|---|---|
| Reactor mean residence time (min) | 287 |
| Reactor temperature (° C.) | 149 |
| Reactor pressure (kPa) | 101 |
| Overall reaction 1113TeCPa conversion (%) | 91.4 |
| Overall 113TCPe reaction yield (mol TCPe/mol TeCPa converted, in %) | 98.7 |
| Overall 113TCPe yield in % including the all process steps described in Example | 97.8 |

The full impurity profile of the product of the above-described embodiment is presented in the following table. The figures are given as a weighted average of the profiles for the product obtained in line 15 in FIG. 1 and line 213.1 in FIG. 3.

| Compound | Wt % |
|---|---|
| Perchloroethylene | 0.006 |
| 3,3,3-Trichloropropene | 0.038 |
| 1,1,3-Trichloropropene | 99.347 |
| 2,3-dichloropropanoyl chloride | 0.045 |
| 1,1,3,3-Tetrachloropropene | 0.004 |
| 1,1,1,3-Tetrachloropropane | 0.322 |
| unknown | 0.238 |

As can be seen, when the dehydrochlorination reaction is controlled such that the molar ratio of 1,1,3-trichloropropene:1,1,1,3-tetrachloropropane does not exceed 30:70, the process of the present invention can be operated to produce highly pure chlorinated alkene material with the very high selectivity and in high yield. Of note is that 3,3,3-Trichloropropene is only formed in trace amounts. This is particularly advantageous as 3,3,3-Trichloropropene is a very reactive olefin contaminant with a free induced (activated) double bond and can be a precursor of highly problematic oxygenated impurities.

Example 3

Alkene:Alkane Ratio in Reaction Mixture

These examples were conducted using the apparatus and techniques employed in Example 1 above, except where otherwise stated. In each of these trials, the reaction progress was controlled such that there was a different ratio between 1,1,3-Trichloropropene:1,1,1,3-Tetrachloropropane in the reaction mixture present in the reactor (equip. 3) reaction mixture (stream 7) in each trial. The amount of dosed catalyst FeCl3 was controlled to maintain the reaction conversion rate at about 90%. The influence of different levels of 113TCPe in reaction mixture on the heavy oligomers formation and catalyst deactivation is shown in the following tables:

| | Heavy Oligomer Formation | | | | | |
|---|---|---|---|---|---|---|
| | 3-1 | 3-2 | 3-3 | 3-4 | 3-5 | 3-6 |
| Calculated TCPe:TeCPa molar ratio in reac. mix | 23:77 | 22:78 | 34:66 | 43:57 | 46:54 | 43:57 |
| TCPe (%) in reaction mixture | 18.95 | 18.25 | 27.6 | 34.54 | 32.01 | 34.31 |
| Heavy oligomers/TCPe | 0.36% | 0.40% | 1.05% | 1.57% | 2.87% | 2.54% |
| | 3-7 | 3-8 | 3-9 | 3-10 | 3-11 | 3-12 |
| Calculated TCPe:TeCPa molar ratio in reac. Mix | 39:61 | 37:63 | 40:60 | 39:61 | 38:62 | 39:61 |

-continued

| Heavy Oligomer Formation | | | | | | |
|---|---|---|---|---|---|---|
| TCPe (%) in reaction mixture | 32.1 | 29.94 | 32.84 | 31.46 | 30.56 | 31.83 |
| Heavy oligomers/TCPe | 1.56% | 1.79% | 1.65% | 1.01% | 1.47% | 1.55% |

| Catalyst Deactivation | | | | | | |
|---|---|---|---|---|---|---|
| | 3-1 | 3-2 | 3-3 | 3-4 | 3-5 | 3-6 |
| TCPe (%) in reaction mixture | 18.95 | 22.36 | 27.6 | 34.54 | 32.01 | 34.31 |
| Calculated TCPe:TeCPa molar ratio in reac. mix | 23:77 | 22:78 | 34:66 | 43:57 | 46:54 | 43:57 |
| Required conc. of FeCl3 in feedstock | 26.5 | 26.5 | 66 | 101 | 116 | 78 |
| | 3-7 | 3-8 | 3-9 | 3-10 | 3-11 | 3-12 |
| TCPe (%) in reaction mixture | 32.1 | 29.94 | 32.84 | 31.46 | 30.56 | 31.83 |
| Calculated TCPe:TeCPa molar ratio in reac. Mix | 39:61 | 37:63 | 40:60 | 39:61 | 38:62 | 39:61 |
| Required conc. of FeCl3 in feedstock | 132 | 132 | 105 | 177 | 106 | 74 |

As can be seen from this example, when the specific apparatus and techniques employed, an increase in the molar ratio of the product to the starting material (increased amount of the product in the reaction mixture) corresponds to an increase in the formation of heavy oligomers. Further, if the 1,1,3-Trichloropropene concentration is high, catalyst deactivation was also observed.

Example 4

Compatibility of the Product Fluid with Various Materials

An Erlenmeyer glass flask was filled with pure distilled 1,1,3-Trichloropropene with purity of >99%. The test construction material sample was immersed in the liquid and the system was closed with a plastic plug.

Samples of the Trichloropropene were regularly taken from the flask. The construction material samples were weighed before and after trail. The temperature of the liquid was ambient laboratory conditions, around 25° C.

The major changes in the quality of the Trichloropropene are shown in the following table, as a % change in purity:

| | Feedstock | 4-1 | 4-2 | 4-3 | 4-4 |
|---|---|---|---|---|---|
| Trial duration | 0 day | 29 days | 29 days | 30 days | 30 days |
| Construction Material | | CS | SS 1.4541 | Ti | C-276 |
| 1,1,3-Trichloropropene - relative change (%) | 0 | −53.75 | −3.70 | −3.27 | −0.67 |
| Sum of oligomers (%) | 0 | 42.68 | 0.20 | 0.32 | 0.01 |

CS=carbon steel, SS=stainless steel, Ti=Titanium, C-276=Hastelloy C-276

In a second set of trials, an Erlenmeyer glass flask equipped with a back cooler and oil heating bath with controlled temperature was filled with pure distilled 1,1,3-Trichlorpropene with a purity of >99%. The test material sample was immersed in the liquid and the system was partially closed using a plastic plug. Samples of Trichloropropene were regularly taken from the flask. The material samples were weighed before and after trail. The temperature of the liquid was controlled at 100° C. The major changes in the liquid Trichloropropene are shown in the following table:

| | feedstock | 4-5 | 4-6 | 4-7 | 4-8 |
|---|---|---|---|---|---|
| Trial duration | 0 day | 5 hours | 48 hours | 5 hours | 48 hours |
| Construction Material | | Glass as material of flask | | Impregnated graphite | |
| 1,1,3-Trichloropropene - relative change (%) | 0 | −0.32 | −2.31 | −0.30 | −2.00 |
| Sum of oligomers (%) | 0 | 0.05 | 0.28 | 0.05 | 0.34 |
| | feedstock | 4-9 h | 4-10 | 4-11 | 4-12 |
| Trial duration | 0 hours | 5 hours | 48 hours | 5 hours | 48 hours |
| Construction Material | | SS 1.4341 | | SS 1.4541 | |
| 1,1,3-Trichloropropene - relative change (%) | 0 | −0.54 | −3.08 | −0.51 | −2.80 |
| Sum of oligomers (%) | 0 | 0.27 | 1.01 | 0.29 | 1.29 |

As can be seen from this example, the use of carbon steel appeared to be challenging as it is not compatible with the process fluid consisting of 1,1,3-Trichlorpropene. Stainless steel and titanium have also poor performance, resulting in the formation of significant amounts of oligomers are formed. From the tested metal materials, the Ni-alloy Hastelloy C-276 has excellent results. It can be seen also that glass (or enamel) and other non-metallic material, such as phenolic resin impregnated graphite, are also more suitable.

Example 5

Problematic Chlorinated Alkene Impurities

In many downstream reactions in which chlorinated alkenes are used as starting materials, the presence of oxygenated organic impurities is problematic. This example demonstrates that certain impurities have a surprising propensity to form such compounds.

A four neck glass flask equipped with a stirrer, thermometer, back cooler, feed and discharge neck and cooling bath was filled with water and chlorine gas was bubbled into the water to produce a weak solution of hypochlorous acid. When an appropriate amount of chlorine had been introduced into the water, a feedstock consisting obtained from the process of Example 1 comprising 1,1,3-Trichloropropene with a purity of 98.9% was slowly dropped into the prepared solution of hypochlorous acid for a period of 90 min and cooled. The pressure was atmospheric and temperature close to 20° C. The same procedure was repeated with 3,3,3-Trichlorpropene having a purity of 68.1%. After reaction completion the systems formed bi-phasic mixtures. The organic phase (product) was extracted and then analyzed by GC. The results are shown in the following table:

|  | 5-1 | | 5-2 | |
| --- | --- | --- | --- | --- |
| Hypochlorination of Trichloropropenes | Feedstock (%) | Product (%) | Feedstock (%) | Product (%) |
| 3,3,3-Trichloropropene | 68.063 | 33.544 | 0.024 | 0.023 |
| 1,1,3-Trichloropropene | 21.772 | 16.651 | 98.922 | 91.374 |
| 1,1,1,2,3-Pentachloropropane | | 20.942 | | 6.800 |
| 1,1,1,3-Tetrachloropropan-2-ol | | 12.792 | | 0.018 |

As can be seen from this example, 1,1,3-Trichlorpropene reacts with chlorine in water to produce 1,1,1,2,3-Pentachloropropane, while 3,3,3-Trichloropropene reacts significantly to produce corresponding tetrachlorohydrines, especially 1,1,1,3-Tetrachloropropan-2-ol.

In other words, 1,1,3-Trichlorpropene reacts to produce a product of commercial interest, while 3,3,3-Trichloropropene reacts to the produce an oxygenated impurity which cannot be easily removed from the 1,1,1,2,3-Pentachloropropane. As is apparent from Examples 1 and 2 above, the processes of the present invention can be advantageously employed to produce 1,1,3-trichloropropene resulting in the formation of only trace amounts of 3,3,3-trichloropropene.

The invention claimed is:

1. A process for preparing a chlorinated alkene comprising contacting a chlorinated alkane with a catalyst in a dehydrochlorination zone to produce a liquid reaction mixture comprising the chlorinated alkane and the chlorinated alkene, wherein the chlorinated alkane starting material contains less than 2000 ppm chlorinated alkane impurities or chlorinated alkene impurities, and wherein the impurities have a boiling point that is equal to or greater than the boiling point of the chlorinated alkane, the chlorinated alkene, or both the chlorinated alkane and the chlorinated alkene, and extracting chlorinated alkene from the reaction mixture, wherein the concentration of the chlorinated alkene in the reaction mixture present in the dehydrochlorination zone is controlled such that the molar ratio of chlorinated alkene:chlorinated alkane is from 1:99 to 50:50.

2. The process of claim 1, wherein the molar ratio of chlorinated alkene:chlorinated alkane in the reaction mixture is from 5:95 to 50:50.

3. The process of claim 1, wherein the molar ratio of chlorinated alkene:chlorinated alkane in the reaction mixture is from 5:95 to 30:70.

4. The process of claim 1, wherein the chlorinated alkane contacted with the catalyst in the dehydrochlorination zone has a purity of about 98.5% or higher.

5. The process of claim 1, wherein the chlorinated alkene is extracted from the reaction mixture on a continuous basis.

6. The process of claim 1, wherein extraction of the chlorinated alkene from the reaction mixture is achieved by distillation.

7. The process of claim 6, wherein the distillation is performed in distillation apparatus in fluid communication with the dehydrochlorination zone.

8. The process of claim 7, wherein the distillation apparatus is coupled to the dehydrochlorination zone.

9. The process of claim 1 where liquid reaction mixture is extracted from the dehydrochlorination zone and subjected to distillation using apparatus remote from the dehydrochlorination zone.

10. The process of claim 6, wherein the distillate comprises gaseous hydrochloric acid as an impurity which is extracted therefrom.

11. The process of claim 1, wherein the operating temperature in the dehydrochlorination zone is about 70° C. to about 250° C.

12. The process of claim 1, wherein the operating temperature in the dehydrochlorination zone is about 120° C. to about 170° C.

13. The process of claim 1, further comprising contacting a mixture comprising chlorinated alkene, catalyst and chlorinated alkane starting material with an aqueous medium in an aqueous treatment zone.

14. The process of claim 13, wherein the pH of the mixture in the aqueous treatment zone, following the addition of acid, is about 4 or lower.

15. The process of claim 13, wherein the mixture is contacted with a haloalkane extraction agent.

16. The process according to claim 13, wherein a biphasic mixture is formed in the aqueous treatment zone and an organic phase comprising chlorinated alkane and chlorinated alkene is extracted from the biphasic mixture.

17. The process according to claim 16, wherein chlorinated alkene is extracted from the organic phase.

18. The process according to claim 1, wherein the catalyst comprises metallic iron, ferrous chloride and/or ferric chloride.

19. The process according to claim 1, wherein the chlorinated alkene is 1,1,3-trichloropropene.

20. The process according to claim 1, wherein the chlorinated alkane is 1,1,1,3-tetrachloropropane.

21. The process of claim 1, wherein all surfaces of the apparatus in which the process is carried out with which any chlorinated alkene-containing mixture will contact during use of that apparatus have an iron content of about 20% or less, and/or are formed from non-metallic materials.

22. The process of claim 1, wherein the chlorinated alkene produced is 1,1,2,3-tetrachloropropene.

23. The process of claim 1, wherein the chlorinated alkene produced is 1,1,3,3-tetrachloropropene.

24. The process according to claim 21, wherein the non-metallic materials are selected from enamel, glass, impregnated graphite, silicium carbide and/or plastics materials.

25. The process according to claim 24, wherein the impregnated graphite is impregnated with phenolic resin.

26. The process according to claim 24, wherein plastic materials are selected from polytetrafluoroethylene, perfluoroalkoxy, polyvinylidene fluoride or any combination thereof.

* * * * *